United States Patent [19]

Randin

[11] Patent Number: 4,802,848
[45] Date of Patent: Feb. 7, 1989

[54] PARAPULPER RESTORATIVE PIN AND DRIVER ASSEMBLY

[75] Inventor: Jean-Claude Randin, Ballaigues, Switzerland

[73] Assignee: Les Fils D'Auguste Maillefer Societe Anonyme A Ballaigues, Switzerland

[21] Appl. No.: 70,061

[22] Filed: Jul. 6, 1987

[30] Foreign Application Priority Data

Jul. 7, 1986 [CH] Switzerland .................. 2.735/86

[51] Int. Cl.$^4$ .............................................. A61C 5/04
[52] U.S. Cl. .................................... 433/225; 433/128; 433/134
[58] Field of Search ............... 433/225, 102, 147, 128, 433/134

[56] References Cited

U.S. PATENT DOCUMENTS

| | | | |
|---|---|---|---|
| 3,369,298 | 2/1968 | Weissman et al. | 433/128 |
| 4,053,982 | 10/1977 | Weissman | 433/225 |
| 4,299,571 | 11/1981 | McSpadden | 433/102 |
| 4,451,237 | 5/1984 | Filhol | 433/225 |
| 4,692,116 | 9/1987 | Filhol | 433/225 |

FOREIGN PATENT DOCUMENTS 2709120  9/1977  Fed. Rep. of Germany ...... 433/225

Primary Examiner—John J. Wilson
Attorney, Agent, or Firm—Silverman, Cass, Singer & Winburn, Ltd.

[57] ABSTRACT

The parapulper restorative pin comprises a stem provided with a handle permitting to operate it manually, the dentist rotating this handle by gripping it between his fingers. This handle is provided with four longitudinal grooves constituting holds for four longitudinal fingers provided at the front end of a stem constituting a driving member intended to be connected to a motor driving mechanism, for example a dental engine. The engagement of the fingers with the grooves of the handle not only renders the stem of the driving member angularly rigid with the stem of the pin but, moreover, renders these two elements also rigid axially, owing to the fact that the said engagement is a friction fit, that facilitates the presentation of the pin opposite the hole of the dental root into which it has to be screwed.

1 Claim, 1 Drawing Sheet

PARAPULPER RESTORATIVE PIN AND DRIVER ASSEMBLY

BACKGROUND OF THE INVENTION

1. Field of the Invention

This invention relates to a parapulper restorative pin for use in dentistry comprising a stem, an end of which is threaded and which is provided with a weakened breaking zone.

This invention relates also to a driving member for such a pin provided with a handle ensuring the connection between it and a motor driving device.

Further, this invention relates also to an assembly constituted on the one hand with a restorative pin for use in dentistry comprising a stem one end of which is threaded and which is provided with a weakened breaking zone and which carries, at its opposite end, a handle permitting to operate it manually, and on the other hand with a driving member ensuring the connection between the said restorative pin and a motor driving device.

2. Description of the Prior Art

Contrarily to that generally designated by the names of "pins" or "root-posts", the parapulper restorative pins are not mounted in the root canal but in the dentine or in the periphery of the root canal. Thus, they can be used even in teeth which have not been previously devitalized.

The parapulper restorative pins for use in dentistry serve to the mounting and for the reinforcement of obturations of recesses in natural teeth or for the armature of reconstitutions of dental crowns which are impaired. (One understands by "obturation" not the operation of obturating but the material of obturation occupying the cavity). These restorative pins are constituted by a threaded stem which is screwed into the root, which has been previously prepared to this effect, and which shows a weakened breaking zone permitting the dentist to break the stem at the desired length, the portion going beyond the root serving to the anchoring and for reinforcement of the obturation or as an armature of the reconstitution of a stump of crown.

The screwing of these pins in the dentine is effected either by hand, in which case the rear end of the stem is provided with a handle that is gripped by the dentist between his fingers for rotating it, or mechanically, in which case the rear end of the stem is provided with means serving as a hold to a driving member which is secured to the handpiece of the dentist.

SUMMARY OF THE INVENTION

The object of the present invention is to increase the flexibility of use of the restorative pins while permitting them to be inserted either manually or mechanically, by means of a motor driving device.

This object is obtained because of the fact that the restorative pin according to the invention is characterized by the fact that includes both a handle permitting to operate it manually and means constituting a hold for a driving member of a motor driving device permitting to drive it mechanically.

This object is also reached owing to the fact that the driving member according to the invention is characterized by the fact that it comprises a stem ending at one of its ends by a portion arranged in such a way as to engage the handle of the restorative pin, this portion showing a conformation which is reciprocal of the said handle so that, once the inter-engagement is effected, the driving member is angularly rigid with the handle of the pin.

This object is also reached owing to the fact that the assembly of the restorative pin and a driving member is characterized by the fact that the handle of the pin is arranged in such a way as to constitute a hold for one of the ends of the driving member arranged in such a way as to engage the handle and which shows a conformation which is reciprocal of this of the driving member so that once the inter-engagement is effected, the driving member is angularly rigid with the handle of the pin.

DESCRIPTION OF THE PREFERRED EMBODIMENTS

Figure 1:
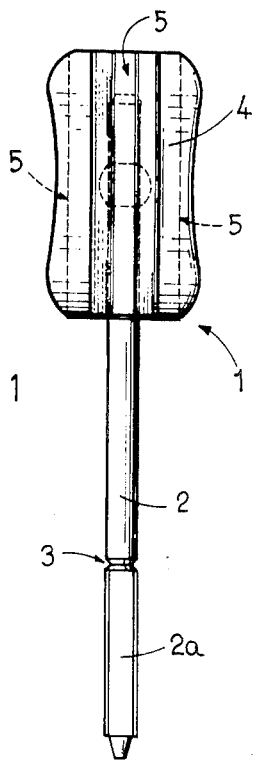
FIG. 1 is an elevational view of a parapulper restorative pin for use in dentistry.
Figure 2:
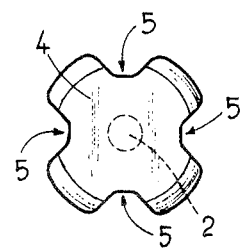
FIG. 2 is an end view of the rear end of this pin.
Figure 3:
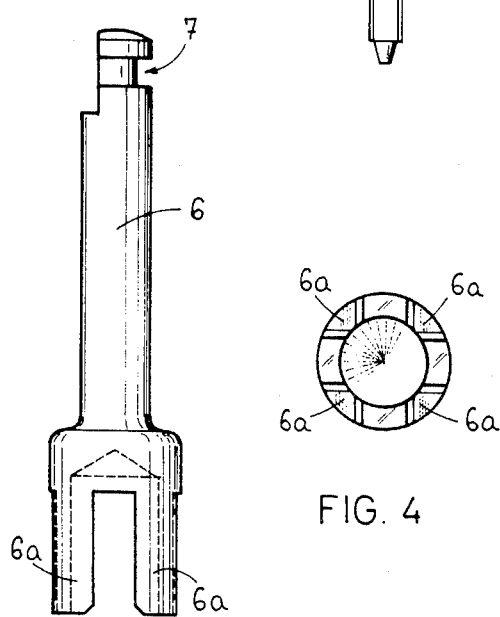
FIG. 3 is an elevational view of a driving member for the restorative pin of FIGS. 1 and 2.
Figure 4:
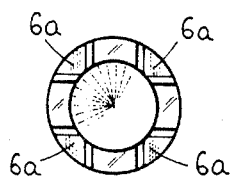
FIG. 4 is an end view of the front end of this driving member.
Figure 5:
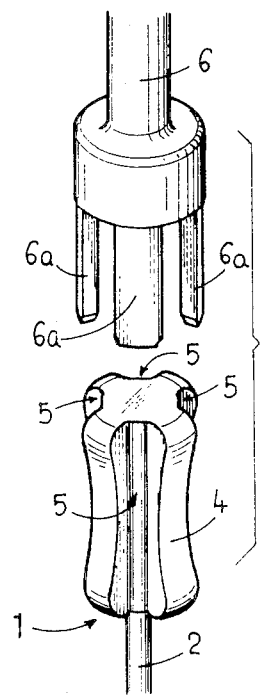
FIG. 5 is a perspective view of a part of the restorative pin of FIGS. 1 and 2 and of a part of the driving member of FIGS. 3 and 4.

The parapulper restorative pin illustrated in FIGS. 1 and 2, generally designated by 1, comprises a stem 2 the front end 2a of which is threaded and which is provided with an annular groove 3 constituting a weakened breaking zone.

This stem 2 is provided, at its rear end, with a handle 4 constituted by a revolution body which allows the pin to be screwed into a dental root previously prepared while rotating the handle 4 between one's fingers.

The handle of the pin as disclosed and represented is provided with four longitudinal grooves 5, arranged at 90° from each other, intended to receive each one of the four longitudinal fingers 6a of the front end of a stem 6 constituting a driving member permitting the mechanical driving of the pin. The rear end of this stem shows, at 7, a configuration which permits to engage it into the handpiece of a dental engine in view of ensuring the mechanical driving of the pin.

It is to be noted that the arrangement is such that the fingers 6a of the driving member engage by a friction fit with the handle 4 of the restorative pin 1 so that the latter is not only rendered angularly rigid with the driving member but also axially, that facilitates its presentation, before screwing, opposite the hold bored in the root for receiving it.

The number of the longitudinal grooves 5 of the handle 4 of the pin and of the longitudinal fingers 6a of the stem 6 of the driving member could be different from four, either two or three, for example, these grooves and these fingers being distributed angularly regularly around the axis of the pin and of the driving member, respectively.

One could also consider the case where the handle 4 of the pin would be provided with only one longitudinal groove with which would engage a longitudinal inner rib of the ending portion, tubular, of the driving member, engaged on the handle of the pin.

Owing to the present arrangement, the restorative pin 1 can be screwed either manually by means of the handle 4 or mechanically by means of the driving member 6 which is itself driven by a motor driving device.

I claim:

1. An assembly on the one hand having a parapulper restorative pin for use in dentistry having a stem one end of which is threaded, which includes a weakened breaking zone and which carries, at its opposed end, a handle permitting to operate it manually, and on the other hand a driving member ensuring the connection between said restorative pin and a motor driving device, in which said handle of said pin is arranged in such a way as to constitute a hold for one of the ends of said driving member arranged in such a way as to engage said handle and which includes a conformation which is reciprocal of said driving member so that once the interengagement is effected, said driving member is angularly rigid with said handle of said pin and said handle of said pin is provided with several longitudinal grooves distributed angularly regularly around the axis of said pin, said end of said driving member cooperating with said handle being provided with a corresponding number of longitudinal fingers, also distributed angularly regularly around the axis of said driving member, engaging each one of said longitudinal grooves of said handle of said pin.

* * * * *